United States Patent [19]

Parker et al.

[11] Patent Number: 5,688,834
[45] Date of Patent: Nov. 18, 1997

[54] CATALYSTS WHICH STABILIZE HYDROHALOCARBON BLOWING AGENT IN POLYURETHANE FOAM FORMULATIONS

[75] Inventors: Robert Christian Parker, Hamburg; Timothy Rech Demmin, Grand Island, both of N.Y.

[73] Assignee: AlliedSignal, Inc., Morristown, N.J.

[21] Appl. No.: 777,876

[22] Filed: Oct. 15, 1991

Related U.S. Application Data

[63] Continuation-in-part of Ser. No. 752,396, Aug. 30, 1991, abandoned.

[51] Int. Cl.$^6$ .................... C08J 9/14; C08G 18/16; C08G 18/18; C08G 18/32
[52] U.S. Cl. .................... 521/118; 521/115; 521/124; 521/126; 521/127; 521/128; 521/129; 521/131; 521/163; 521/164; 521/166; 521/170; 252/182.2
[58] Field of Search ............... 521/118, 126, 521/127, 128, 129, 131, 163, 164, 166, 170, 124, 115; 252/182.2

[56] References Cited

U.S. PATENT DOCUMENTS

| | | | |
|---|---|---|---|
| 4,386,166 | 5/1983 | Peterson et al. | 521/112 |
| 4,945,119 | 7/1990 | Smits et al. | 521/131 |
| 4,986,930 | 1/1991 | Lund et al. | 521/131 |
| 4,992,483 | 2/1991 | Sylvester | 521/131 |
| 5,034,426 | 7/1991 | Casey et al. | 521/163 |
| 5,114,980 | 5/1992 | Lii et al. | 521/118 |
| 5,137,929 | 8/1992 | Demmin et al. | 521/107 |
| 5,216,040 | 6/1993 | Kuroishi et al. | 521/128 |
| 5,395,859 | 3/1995 | Demmin et al. | 521/125 |
| 5,561,171 | 10/1996 | Demmin et al. | 521/118 |

FOREIGN PATENT DOCUMENTS

| | | |
|---|---|---|
| 0355713 | 2/1990 | European Pat. Off. |
| 0300366 | 1/1989 | France |

*Primary Examiner*—Rabon Sergent
*Attorney, Agent, or Firm*—Melanie L. Brown; Colleen D. Szuch; Jay P. Friedenson

[57] ABSTRACT

The present invention relates to foam compositions which are expanded with hydrohalocarbon blowing agents in the presence of catalysts which result in a decreased amount of decomposition of the hydrohalocarbon blowing agents to haloalkenes during the polymerization. Thus, the present invention provides compositions comprising polyisocyanate, polyol, hydrohalocarbon blowing agent, surfactant, and at least one catalyst for polymerization of the polyisocyanate and polyol wherein the catalyst is less volatile than N,N-dimethylcyclohexylamine or the catalyst is a tertiary amine having at least one isocyanate-reactive functionality selected from the group consisting of —OH and —NH— and the catalyst results in a decreased amount of decomposition of the hydrohalocarbon blowing agents to haloalkenes during polymerization of the polyisocyanate and the polyol and especially during use of the foam samples at a temperature of at least about 54° C.

9 Claims, No Drawings

CATALYSTS WHICH STABILIZE HYDROHALOCARBON BLOWING AGENT IN POLYURETHANE FOAM FORMULATIONS

This application is a continuation-in-part application of Ser. No. 752,396 filed Aug. 30, 1991, now abandoned.

This invention relates to closed cell polyurethane foams expanded with hydrohalocarbons in the presence of specific polymerization catalysts which also serve to maintain the chemical integrity of the hydrohalocarbon during exposure of the foams to temperatures above ambient temperature.

BACKGROUND OF THE INVENTION

It is well known to those skilled in the art that polyurethane foams can be prepared by reacting and foaming a mixture of ingredients, consisting in general of an organic polyisocyanate (including diisocyanate) and an appropriate amount of polyol or mixture of polyols in the presence of a volatile liquid blowing agent, which is caused to vaporize by the heat liberated during the reaction of polyisocyanate and polyol. It is also well known that this reaction and foaming process can be enhanced through use of amine and metal carboxylate catalysts as well as surfactants. The catalysts ensure adequate curing of the foam while the surfactants regulate and control cell size.

In the class of foams known as low density rigid polyurethane foam, the blowing agent of choice has been trichlorofluoromethane, $CCl_3F$ (known in the art as CFC-11). These types of foams are closed-cell foams in which the CFC-11 vapor is encapsulated or trapped in the matrix of closed cells. They offer excellent thermal insulation, due in part to the very low thermal conductivity of CFC-11 vapor, and are used widely in insulation applications, e.g. in refrigeration units and in hot water tanks. Generally, 1 to 60 parts by weight and typically, 15 to 40 parts by weight of blowing agent per 100 parts by weight polyol are used in rigid polyurethane formulations.

In 1985, about 140 MM lbs. of blowing agents including CFC-11 and dichlorodifluoromethane (known in the art as CFC-12) were used in the U.S. to produce all types of insulation foams. Of this total volume, about 70% or 100 MM lbs. were used to make polyurethane foam. Closed-cell polyurethane foam is the most energy efficient insulating material available having an R value of approximately 7.2 per inch whereas fiberglass has an R value of approximately 3.1 per inch.

Closed-cell polyurethane foams are widely used for insulation purposes in building construction and in the manufacture of energy efficient electrical appliances. Poured and sprayed polyurethane foams are also used in construction. Sprayed polyurethane foams are widely used for insulating large structures such as storage tanks, etc. Pour-in-place polyurethane foams are used, for example, in appliances such as refrigerators and freezers plus they are used in making refrigerated trucks and rail cars.

In the early 1970's, concern began to be expressed that the stratospheric ozone layer (which provides protection against penetration of the earth's atmosphere by ultraviolet radiation) was being depleted by chlorine atoms introduced to the atmosphere from the release of fully halogenated chlorofluorocarbons. These chlorofluorocarbons are widely used as propellants in aerosols, as blowing agents for foams, as refrigerants, and as cleaning/drying solvent systems. Because of the great chemical stability of fully halogenated chlorofluorocarbons, according to the ozone depletion theory, these compounds do not decompose in the earth's lower atmosphere but reach the stratosphere where they slowly degrade liberating chlorine atoms which in turn react with the ozone.

During the period of 1978 to the present, much research was conducted to study the ozone depletion theory. Because of the complexity of atmospheric chemistry, many questions relating to this theory remain unanswered. However, if the theory is valid, the health risks which would result from depletion of the ozone layer are significant. This, coupled with the fact that world-wide production of chlorofluorocarbons has increased, has resulted in international efforts to reduce chlorofluorocarbon use. Most recently, the United States Clean Air Act calls for total phaseout of CFC's by the year 2000.

Because of this proposed reduction in availability of fully halogenated chlorofluorocarbons such as CFC-11 and CFC-12, more environmentally acceptable products are urgently needed.

As early as the 1970's with the initial emergence of the ozone depletion theory, it was known that the introduction of hydrogen into previously fully halogenated chlorofluorocarbons markedly reduced the chemical stability of these compounds. Hence, these now destabilized compounds would be expected to degrade in the lower atmosphere and not reach the stratosphere and the ozone layer. Table I lists the ozone depletion potentials for a variety of fully and partially halogenated halocarbons. Greenhouse potential data (potential for reflecting infrared radiation (heat) back to earth and thereby raising the earth's surface temperature) are also shown. In Table I, the ozone depletion potentials and greenhouse potentials were calculated relative to CFC-11.

TABLE I

| Blowing Agent | Ozone Depletion Potential | Greenhouse Potential |
|---|---|---|
| CFC-11($CFCl_3$) | 1.0 | 1.0 |
| CFC-12($CF_2Cl_2$) | 1.0 | 3.1 |
| HCFC-22($CHF_2Cl$) | 0.05 | 0.36 |
| HCFC-123($CF_3CHCl_2$) | 0.015 | 0.02 |
| HCFC-141b($CFCl_2CH_3$) | 0.15 | 0.15 |

Halocarbons such as HCFC-123 and HCFC-141b are environmentally acceptable in that they theoretically have minimal effect on ozone depletion.

Organic substances which bear a hydrogen on one carbon and a halogen (F, Cl, Br, I) on an adjacent carbon, will undergo so-called elimination reactions, under the influence of bases or acids, to produce haloalkenes and hydrogen halides or products from the combination of the hydrogen halide with the base, known as salts.

Therefore, in view of the fact that some of the major and many of the minor components, i.e., polyols and catalysts (amines, metal salts), are of known basic character, dehydrohalogenation of the above mentioned hydrohalocarbons might occur. Examples of such reactions are as follows:

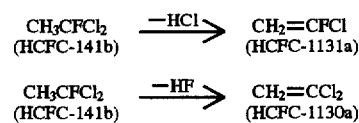

$$\text{CF}_3\text{CHCl}_2 \xrightarrow{-\text{HF}} \text{CF}_2=\text{CCl}_2$$
(HCFC-123)  (HCFC-1112a)

Many of these haloalkenes possess unknown properties and it is therefore desirable to hold their formation to a minimum as a precautionary measure.

Tests performed using the above hydrohalocarbons as blowing agents, in typical foam formulations now in commercial use, revealed that the haloalkenes can be found in the cells of the cured foam at concentrations as high as 10,000 parts per million/weight relative to the blowing agent.

Stabilizers have been added to hydrohalocarbons to inhibit or minimize the generation and buildup of degradation products. For example, Kokai Patent Publication 103,843 published May 22, 1986 teaches that the addition of benzotriazole stabilizes 1,2-dichloro-1-fluoroethane when it is exposed to metallic surfaces in the presence of hydroxylic solvents, e.g. water or alcohols. Kokai Patent Publication 132,539 published May 25, 1989 teaches the addition of nitro compounds, phenols, amines, ethers, amylenes, esters, organic phosphites, epoxides, and triazoles to 1,2-dichloro-1-fluoroethane containing compositions in order to stabilize the compositions upon contact with metallic cleaning apparatus. Kokai Patent Publication 139,539 published Jun. 1, 1989 teaches the addition of nitro compounds, phenols, amines, ethers, amylenes, esters, organic phosphites, epoxides, furans, alcohols, ketones, and triazoles to 1,2-dichloro-1,1,2-trifluoroethane containing compositions in order to stabilize the compositions upon contact with metallic cleaning apparatus. U.S. Pat. No. 4,861,926 teaches that 1,1,1-trichloroethane can be stabilized with mixtures of epoxybutane, nitromethanes, 2-methylfuran, and methyl acetate in textile dry cleaning and metal degreasing applications. The Abstract of Japanese 2,204,424 published Aug. 14, 1990 teaches that hydrochlorofluoropropanes in the presence of steel are thermally stabilized by adding nitro compounds, phenols, amines, ethers, esters, epoxides, alcohols, ketones, or triazoles.

Specialized chemical additives are often present in low density rigid polyurethane foams to enhance certain performance features of the foam, e.g., flame retardants, antioxidants, and solubilizing surfactants. Such additives are dissolved in a formulation component or pre-mix prior to foam production. Flame retardants include halocarbons, e.g., chloroalkyl phosphate esters, polybromoalkanes, or polybromoaromatics. Antioxidants are typically phosphite esters. Solubilizing agents commonly used are ethoxylated nonylphenols.

SUMMARY OF THE INVENTION

We have found that the use of certain catalysts, in addition to catalyzing the polymerization of polyisocyanates and polyols, results in a decreased amount of decomposition of hydrohalocarbon blowing agent to haloalkenes during polymerization of the polyisocyanates with the polyols, and especially during use of the foam at elevated temperatures. Preferably, the use of the catalysts, in addition to catalyzing the polymerization of polyisocyanates and polyols, results in a decreased amount of decomposition of hydrohalocarbon blowing agent to haloalkenes during polymerization of the polyisocyanates with the polyols, and especially during use of the foam at a temperature of at least about 54° C.

Although not wishing to be bound by theory, we believe that the commonly used amine catalysts induce a classical dehydrohalogenation of the hydrohalocarbon blowing agent, not only during polymerization of the polyisocyanates and the polyols where high temperatures and reactive intermediates may be contributing factors, but also during long term exposure of the foam to application temperatures above ambient temperature. In most polyurethane foams, the majority of dehydrohalogenation occurs during prolonged foam exposure at elevated temperatures, not during foam formation. We believe that the major cause of dehydrohalogenation in these cases is due to a simple gas phase elimination of hydrohalic acid induced by the tertiary amine polyurethane catalyst, e.g. N,N-dimethylcyclohexylamine, which remains in moderate concentration in the vapor phase above the solid polymer.

We have found that at a given temperature, any polyurethane catalyst that is less basic and/or less volatile than N,N-dimethylcyclohexylamine will induce substantially less decomposition of the hydrohalocarbon blowing agent to haloalkene. Polyurethane catalysts which are less volatile or non-volatile are useful in practicing the present invention because these catalysts are substantially absent from the vapor phase above the solid polymer. In addition to less volatile or non-volatile catalysts, non-fugitive tertiary amine catalysts which contain at least one isocyanate-reactive functionality selected from the group consisting of —OH and —NH— are useful in practicing the present invention because these catalysts become bound to the polyurethane chains and thus, are substantially absent from the vapor phase above the solid polymer. Thus, any catalyst which is less volatile than N,N-dimethylcyclohexylamine or which is a tertiary amine having at least one isocyanate-reactive functionality selected from the group consisting of —OH and —NH— and also polymerizes the polyisocyanate and polyol is useful in practicing the present invention.

Thus, the present invention provides compositions comprising polyisocyanate, polyol, hydrohalocarbon blowing agent, surfactant, and at least one catalyst for polymerizing the polyisocyanate and polyol wherein the catalyst is less volatile than N,N-dimethylcyclohexylamine or the catalyst is a tertiary amine having at least one isocyanate-reactive functionality selected from the group consisting of —OH and —NH— wherein the use of the catalyst results in a decreased amount of decomposition of the hydrohalocarbon blowing agent to haloalkenes.

N,N-dimethylcyclohexylamine has a boiling point of 158° C. Preferably, a "less volatile than N,N-dimethylcyclohexylamine" catalyst is a catalyst having a boiling point of at least 184° C.; this minimum boiling point is 26° C. higher than the boiling point of N,N-dimethylcyclohexylamine.

Preferably, the catalyst is selected from the group consisting of dialkyltin dicarboxylates and other metal carboxylates such as lead carboxylates; N,N-dialkylbenzylamines; N,N-dialkylarylamines; polyamines; hydroxyalkylamines; and (diaminoaryl) amines.

The term "haloalkenes" as used herein means those organic materials having at least one double bond and at least one halogen atom therein. The haloalkenes which form depend on the hydrohalocarbon blowing agent used. For example, if the blowing agent used is 1,1-dichloro-1-fluoroethane, the haloalkenes which may form include 1,1-dichloroethylene and 1-chloro-1-fluoroethylene. If the blowing agent used is 1,1-dichloro-2,2,2-trifluoroethane, the haloalkene which may form is 1,1-dichloro-2,2-difluoroethylene.

Preferably, the use of the catalyst results in a decreased amount of decomposition of the hydrohalocarbon blowing agent to haloalkenes during polymerization of the polyisocyanate with the polyol and especially during foam use at temperatures above ambient temperatures such that the haloalkenes are present in an amount of less than about 1500 micrograms per gram of the hydrohalocarbon blowing agent. Most preferably, when the hydrohalocarbon blowing agent is 1,1-dichloro-1-fluoroethane, the use of the catalyst results in a decreased amount of 1-chloro-1-fluoroethylene formed during the practice of the present invention to less than about 1000 micrograms per gram of 1,1-dichloro-1-fluoroethane.

Other advantages of the present invention will become apparent from the following description.

DETAILED DESCRIPTION OF THE PREFERRED EMBODIMENTS

Preferred dialkytin dicarboxylates are of the formula $R^1R^2Sn+^2(R^3CO_2—)_2$ where $R^1$ and $R^2$ are the same or different and selected from straight chain and branched alkyl having 1 to 10 carbon atoms; straight chain and branched substituted alkyl and hydroxyalkyl having 2 to 18 carbon atoms containing $—CH_2—CR^4R^5Cl$ where $R^4$ and $R^5$ are the same or different and selected from hydrogen, bromine, chlorine, aryl, and alkyl having 1 to 8 carbons, and preferably, $R^4$ and $R^5$ are both chlorine atoms; and straight chain and branched alkoxyalkyl having 4 to 23 carbon atoms containing $—CH_2—(CH_2)_n—(CO)_a—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 to 3, and a is 0 or 1, and $R^3$ is selected from straight chain and branched alkyl and substituted alkyl and hydroxyalkyl having 1 to 18 carbon atoms and straight chain and branched alkoxyalkyl having 4 to 23 carbon atoms containing $—CH_2—(CH_2)_n—(CO)_a—O—CH_2—CR^4R^5Cl$ where $R^4$ and $R^5$ are the same or different and selected from hydrogen, bromine, chlorine, aryl, and alkyl having 1 to 8 carbons, and preferably, $R^4$ and $R^5$ are both chlorine atoms, n is 1 to 3, and a is 0 or 1.

The foregoing tin catalysts are known and may be prepared by methods known in the art such as the reaction of acid anhydride and dialkyltin oxide or as disclosed by U.S. Pat. No. 2,846,408 or may be obtained from suppliers such as Air Products and Chemicals, Inc. An example of a preferred dialkytin dicarboxylate is dibutyltin dilaurate which is available as DABCO T-12® from Air Products and Chemicals, Inc. Other preferred dialkyltin dicarboxylates are di(2-ethylhexyl)tin di(2-ethylhexanoate) and dihexyltin didecanoate.

Preferred lead carboxylates include lead naphthenate which is available as 24% Lead NAP-ALL®, a 65% by weight lead naphthenate in mineral spirits from Mooney Chemicals, Inc.

Preferred N,N-dialkylbenzylamines are of the formula $R^6R^7N—CH_2—R^8$ where $R^6$ and $R^7$ are the same or different and selected from straight chain and branched alkyl having 1 to 18 carbon atoms; straight chain and branched substituted alkyl and hydroxyalkyl having 2 to 18 carbon atoms containing $—CH_2—CR^4R^5Cl$ where $R^4$ and $R^5$ are the same or different and selected from hydrogen, bromine, chlorine, aryl, and alkyl having 1 to 8 carbons, and preferably, $R^4$ and $R^5$ are both chlorine atoms; and straight chain and branched alkoxyalkyl having 4 to 23 carbon atoms containing $—CH_2—(CH_2)_n—(CO)_a—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine, n is 1 to 3, and a is 0 or 1; and $R^8$ is selected from aryl and substituted aryl having 6 to 18 carbon atoms and alkoxyaryl having 8 to 28 carbon atoms containing $—(CH_2)_m—(CO)_b—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, m is 0 to 3, and b is 0 or 1.

Some of the foregoing amine catalysts are known and may be prepared by known methods. An example of a preferred N,N-dialkylbenzylamine is N,N-dimethylbenzylamine which is commercially available.

Preferred N,N-dialkylarylamines are of the formula $R^9R^{10}N—R^{11}$ where $R^9$ and $R^{10}$ are the same or different and selected from straight chain and branched alkyl and substituted alkyl having 1 to 18 carbon atoms; straight chain and branched substituted alkyl and hydroxyalkyl having 2 to 18 carbon atoms containing $—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms; and straight chain and branched alkoxyalkyl having 4 to 23 carbon atoms containing $—CH_2—(CH_2)_n—(CO)_a—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 to 3, and a is 0 or 1; and $R^{11}$ is selected from aryl and substituted aryl having 6 to 18 carbon atoms and alkoxyaryl having 8 to 28 carbon atoms containing $—(CH_2)_m—(CO)_b—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, m is 0 to 3, and b is 0 or 1. This group of aniline catalysts may require a co-catalyst such as selected from the other catalyst groups described herein.

The foregoing amine catalysts are known and may be prepared by known methods. Examples of preferred N,N-dialkylarylamines are N,N-dimethylaniline; N,N-diethylaniline; and N,N,N',N'-tetramethyl-1,4-phenylenediamine which are commercially available.

Preferred polyamines are N-substituted triazines of the formula $C_3H_6N_3—[(R^{12}R^{13}C)_nNR^{14}R^{15}]_3$ where $n \geq 2$; $R^{12}$ and $R^{13}$ are the same or different and selected from hydrogen; alkyl having 1 to 18 carbon atoms; substituted alkyl having 2 to 18 carbon atoms containing $—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms; straight chain and branched alkoxyalkyl having 4 to 23 carbon atoms containing $—CH_2—(CH_2)_n—(CO)_a—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 i to 3, and a is 0 or 1; and $R^{14}$ and $R^{15}$ are the same or different and selected from straight chain and branched alkyl having 1 to 18 carbon atoms; straight chain and branched substituted alkyl and hydroxyalkyl having 2 to 18 carbon atoms containing $—CH_2—CR^4R^5Cl$ where $R^4$ and $R^5$ are the same or different and selected from hydrogen, bromine, chlorine, aryl, and alkyl having 1 to 8 carbons, and preferably, $R^4$ and $R^5$ are both chlorine atoms; and straight chain and branched alkoxyalkyl having 4 to 23 carbon atoms containing $—CH_2—(CH_2)_n—(CO)_a—O—CH_2—CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 to 3, and a is 0 or 1.

The foregoing triazine catalysts are known and may be prepared by methods known in the art such as the reaction of formaldehydes and amines or ammonia as taught by U.S. Pat. Nos. 4,025,469 or 2,993,870 or may be obtained from suppliers such as Air Products and Chemicals Inc. The more preferred substituted triazines include hexahydro-1,3,5-tris [3(N,N-dimethylamino)propyl]-1,3,5-triazine which is commercially available from Air Products and Chemicals Inc. as Polycat® 41 and hexahydro-1,3,5-tris[3(N,N-dimethylamino)ethyl]-1,3,5-triazine; hexahydro-1,3,5-tris[3 (N,N-ethylmethylamino)propyl]-1,3,5-triazine; hexahydro-1,3,5-tris[3(N,N-diethylamino)propyl]-1,3,5-triazine; and hexahydro-1,3,5-tris[3(N,N-dimethylamino)butyl]-1,3,5-triazine.

More preferred polyamines are of the formula $R^{16}R^{17}N—R^{18}—N(R^{19})—R^{18}—NR^{16}R^{17}$ wherein $R^{16}$, $R^{17}$, and $R^{19}$ are the same or different and selected from hydrogen and straight chain and branched alkyl having 1 to 18 carbon atoms; cycloalkyl having 5 to 18 carbon atoms; straight chain and branched substituted alkyl and hydroxyalkyl having 2 to 18 carbon atoms containing —$CH_2$—$CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms; and straight chain and branched alkoxyalkyl having 4 to 23 carbon atoms containing —$CH_2$—$(CH_2)_n$—$(CO)_a$—O—$CH_2$—$CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 to 3, and a is 0 or 1; and $R^{18}$ is selected from alkyl having 1 to 18 carbon atoms.

These polyamines are known and may be prepared by methods known in the art such as disclosed by Marxer et al., *Helv. Chim. Acta* 34, 927 (1951) or may be obtained from suppliers. A most preferred polyamine is $(CH_3)_2N$—$CH_2CH_2$—$N(CH_3)$—$CH_2CH_2$—N—$(CH_3)_2$ which is commercially available from Rhein Chemie Division of Mobay as DESMORAPID PV®.

Other more preferred polyamines are of the formula 2,4,6-tris(N,N-dialkylaminomethylphenol) where alkyl is selected from hydrogen and alkyl having 1 to 18 carbon atoms. These amine catalysts are known and may be prepared by methods known in the art. A most preferred polyamine is 2,4,6-tris(N,N-dimethylaminomethylphenol) which is commercially available from Air Products and Chemicals Inc as DABCO TMR-30®.

Preferred hydroxyalkylamines are of the formula $R^{20}R^{21}N$—$CH_2$—$CH(R^{22})(OH)$ where $R^{20}$ and $R^{21}$ are the same or different and selected from straight chain and branched alkyl and substituted alkyl and hydroxyalkyl having 1 to 18 carbon atoms; straight chain and branched substituted alkyl having 2 to 18 carbon atoms containing —$CH_2$—$CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms; and straight chain and branched alkoxyalkyl having 4 to 23 carbon atoms containing —$CH_2$—$(CH_2)_n$—$(CO)_a$—O—$CH_2$—$CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 to 3, and a is 0 or 1; and $R^{22}$ is selected from straight chain and branched alkyl and hydroxyalkyl having 1 to 18 carbon atoms and straight chain and branched substituted alkyl having 6 to 18 carbon atoms containing —$CH_2$—$CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms; and straight chain and branched alkoxyalkyl having 4 to 23 carbon atoms containing —$CH_2$—$(CH_2)_n$—$(CO)_a$—O—$CH_2$—$CR^4R^5Cl$ where $R^4$ and $R^5$ are the same or different and selected from hydrogen, bromine, chlorine, aryl, and alkyl having 1 to 8 carbon atoms, and preferably, $R^4$ and $R^5$ are both chlorine atoms, n is 1 to 3, and a is 0 or 1. The amine catalysts are known and may be prepared by methods known in the art.

Preferred (diaminoaryl)amines are taught by U.S. Pat. No. 5,034,426 which is incorporated herein by reference. Preferably, the diaminobenzamide is used. The most preferred (diaminoaromatic)amines are N,N-bis(3-dimethylaminopropyl)-diaminobenzamide; (2-morpholinoethyl)-diaminobenzamide; N,N-dimethylaminoethyl-N¹-methyl-diaminobenzamide; N¹-(2-methoxyethyl)-N⁴-(diaminobenzoyl)piperazine; N¹-ethyl-N⁴-(diaminobenzoyl)piperazine; N¹-methyl-N⁵-(diaminobenzoyl)-piperazine; and (2-dimethylaminoethoxyethyl)-diaminobenzamide. These catalysts may be prepared by the methods taught by U.S. Pat. No. 5,034,426.

At least one catalyst is used in the present invention. Depending upon the catalysts selected, mixtures of two or more catalysts may be desirable.

In accordance with this invention, any of these catalysts or combinations of these catalysts or their chemical equivalents may be used as described previously to prepare a variety of polyurethane foams by standard techniques known to the art which may include the use of various standard additives such as surfactants, water, fire retardants, and others.

The typically used ratios of polyisocyanate to polyol and of blowing agent to these components may be used in practicing the present invention.

The use of these catalysts will provide rigid foams with significantly reduced levels of haloalkenes formed during polymerization and especially during foam use at elevated temperatures compared to the levels of haloalkenes found when using the catalysts commonly used in the rigid foam industry.

The amount of the catalyst employed in the present invention will vary depending upon the catalyst selected, the application, the type of foam being prepared, the identity of the polyol and other factors, but can readily be determined by anyone skilled in the art. The catalyst is used in an amount sufficient to polymerize the polyisocyanate and the polyol and also result in a decreased amount of decomposition of the hydrohalocarbon blowing agents to haloalkenes during the polymerization.

Examples of polyols used in polyurethane foams include aromatic amino-based polyether polyols such as those based on mixtures of 2,4- and 2,6-toluenediamine condensed with ethylene oxide and/or propylene oxide. These polyols are used in pour-in-place molded foams. Another example is aromatic alkylamino-based polyether polyols such as those based on ethoxylated and/or propoxylated aminomethylated nonylphenol derivatives. These polyols are used in rigid polyurethane spray foams. Another example is sucrose-based polyether polyols such as those based on sucrose derivatives condensed with ethylene oxide and/or propylene oxide. These polyols are used in rigid high and low density foams, for slabstock, froth foams, and molded foams. Polyols are known in the art and may be prepared by known methods or obtained from suppliers.

Examples of polyisocyanates used in polyurethane foams include aromatic diisocyanates such as those based on mixtures of 2,4- and 2,6-toluene diisocyanate; these polyisocyanates are used in specialty foams. Another example is methylene diphenyl diisocyanate (MDI) which typically contains 55% diphenylmethane diisocyanates, 25% triisocyanates, and 20% higher polyisocyanates. Polyisocyanates are known in the art and may be prepared by known methods or obtained from suppliers.

In practicing the present invention, the molar ratio of polyisocyanate to polyol is about 1.1:1. As those skilled in the art know, the use of polyisocyanate to polyol in an amount of about 1.1:1 results in the formation of polyurethane foams.

Any hydrofluorocarbon blowing agent may be used in the present invention. Preferred hydrofluorocarbon blowing agents include 1,1-difluoroethane; 1,2-difluoroethane; 1,1,1-trifluoroethane; 1,1,2-trifluoroethane; 1,1,1,2-tetrafluoroethane; 1,1,2,2-tetrafluoroethane; 1,1,1,2,2-pentafluoroethane; 1,1,1,3-tetrafluoropropane; 1,1,2,3,3-pentafluoropropane; and 1,1,1,3,3-pentafluoro-n-butane.

Any hydrochlorofluorocarbon blowing agent may be used in the present invention. Preferred hydrochlorofluorocarbon blowing agents include 1-chloro-1,2-difluoroethane; 1-chloro-2,2-difluoroethane; 1-chloro-1,1-difluoroethane; 1,1-dichloro-1-fluoroethane; 1-chloro-1,1,2-trifluoroethane; 1-chloro-1,2,2-trifluoroethane; 1,1-dichloro-1,2-difluoroethane; 1-chloro-1,1,2,2-tetrafluoroethane; 1-chloro-1,2,2,2-tetrafluoroethane; 1,1-dichloro-1,2,2-trifluoroethane; 1,1-dichloro-2,2,2-trifluoroethane; and 1,2-dichloro-1,1,2-trifluoroethane. The most preferred hydrochlorofluorocarbon blowing agent is 1,1-dichloro-1-fluoroethane.

Known methods for the preparation of 1,1-dichloro-1-fluoroethane including the reaction of anhydrous hydrogen fluoride with vinylidene chloride or 1,1,1-trichloroethane such as described in commonly assigned U.S. Pat. No. 4,950,816 may be used.

Mixtures of the preferred hydrohalocarbon blowing agents may also be used in the present invention. Preferred mixtures of hydrohalocarbon blowing agents include a mixture of 1,1-dichloro-1-fluoroethane with 1,1-dichloro-2,2,2-trifluoroethane and a mixture of 1,1-dichloro-2,2,2-trifluoroethane with 1,2-dichloro-1,2,2-trifluoroethane.

Examples of surfactants for rigid polyurethane foams are polyether modified polysiloxanes. These silicone surfactants are typically non-hydrolyzable silicone-polyoxyethylene/ polyoxypropylene copolymers. Other examples include non-silicon-containing organic surfactants which are proprietary in structure. Tegostab®B-8404 is a silicone surfactant which is available from Goldschmidt Chemical Company. Other commercially available silicone surfactants include Tegostab®B-8408 which is available from Goldschmidt Chemical Company, Dabco®DC-193 which is available from Air Products and Chemicals, Inc., and L-5420® which is available from Union Carbide. LK®-443 is an organic surfactant which is available from Air Products and Chemicals, Inc.

The present invention also provides a composition of polyol, surfactant, hydrohalocarbon blowing agent, and at least one catalyst wherein the catalyst is less volatile than N,N-dimethylcyclohexylamine or the catalyst is a tertiary amine having at least one isocyanate-reactive functionality selected from the group consisting of —OH and —NH— and the catalyst decreases the amount of decomposition of the hydrohalocarbon blowing agent to haloalkenes.

Thus, the present invention provides a process for preparing polyurethane foams. The process comprises the step of reacting polyol with polyisocyanate in the presence of hydrohalocarbon blowing agent, surfactant, and at least one catalyst for the polymerization of the polyol with the polyisocyanate. The catalyst is less volatile than N,N-dimethylcyclohexylamine or the catalyst is a tertiary amine having at least one isocyanate-reactive functionality selected from the group consisting of —OH and —NH— and the catalyst results in a decreased amount of decomposition of the hydrohalocarbon blowing agent to haloalkenes. The present invention also provides polyurethane foams prepared by the foregoing process. The present invention further provides polyurethane articles prepared by the foregoing process.

It will be evident to those skilled in the art that water may be included in the polyurethane foam formulations to generate carbon dioxide as a supplemental blowing agent by reaction with polyisocyanate. In addition, water generated intermediates can form cross-linked polymeric structures that may enhance physical properties of the final product.

In a more preferred embodiment, the present invention provides polyurethane compositions comprising polyisocyanate, polyol, hydrohalocarbon blowing agent, surfactant, at least one catalyst for the polymerization of the polyisocyanate and polyol, and additive. The catalyst is less volatile than N,N-dimethylcyclohexylamine or the catalyst is a tertiary amine having at least one isocyanate-reactive functionality selected from the group consisting of —OH and —NH— and the catalyst results in a decreased amount of decomposition of the hydrohalocarbon blowing agent to haloalkenes and also the additive is capable of decreasing the amount of decomposition of hydrohalocarbon to haloalkenes during polymerization of the polyisocyanate and the polyol and during foam use at elevated temperatures. Preferably, the result is that the haloalkenes are present in an amount of less than about 1500 micrograms per gram of the hydrohalocarbon blowing agent.

The catalysts described above are useful in this embodiment. The amount of catalyst required depends upon the type of catalyst selected. Preferably, the catalyst is present at an amount of at least about 0.1 part by weight per hundred parts of polyol. More preferably, the catalyst is present at an amount of about 0.1 part to about 5 parts by weight per hundred parts of polyol.

Preferred additives include nitroalkanes; bromoalkanes; bromoalcohols; chloroalcohols; and di(hydroxyalkyl)esters of tetrabromophthalic acid.

Preferred nitroalkanes are of the formula $R^{23}R^{24}CH—NO_2$ where $R^{23}$ is selected from the group consisting of hydrogen, alkyl having 1 to 18 carbon atoms, cycloalkyl, substituted alkyl, aryl, and substituted aryl, and $R^{24}$ is selected from the group consisting of hydrogen and methyl. More preferred nitroalkanes include nitromethane; nitroethane; 1-nitropropane; 2-nitropropane; 1-nitrobutane; nitrocyclohexane; 1-nitrohexane; nitrocyclopentane; and 1-nitropentane. The foregoing nitroalkanes are commercially available.

Preferred bromoalkanes are of the formula $(Br)_aC(H)_b$ where a is 1, 2, 3, or 4 and a+b=4; $(Br)_c(H)_dC—CH(R^{25})_e(R^{26})_f$ where c is 1, 2, or 3, c+d=3, e+f=2, and $R^{25}$ and $R^{26}$ are the same or different and selected from the group consisting of hydrogen, alkyl having 1 to 18 carbon atoms, substituted alkyl, haloalkyl, aryl, and substituted aryl; and $(Br)_aC(R^{27})_b(R^{28})_c(R^{29})_d$ where a is 1, 2, 3, or 4 and a+b+c+d=4 and $R^{27}$, $R^{28}$, and $R^{29}$ are the same or different and selected from the group consisting of hydrogen, linear alkyl having 1 to 18 carbon atoms, substituted alkyl, haloalkyl, aryl, and substituted aryl. More preferred bromoalkanes include bromomethane; dibromomethane; carbon tetrabromide; bromoform; 1,2-dibromobutane; 1,3-dibromobutane; 1,4-dibromobutane; 2,3-dibromobutane; 1,4-dibromo-2,3-butanediol; 2,3-dibromo-1,4-butanediol; 1,4-dibromo-2-butanol; 1,4-dibromo-2-butene; 1,10-dibromodecane; 1,2-dibromoethane; 1,12-dibromododecane; (1,2-dibromoethyl)benzene; 1,7-dibromoheptane; and 1,6-dibromohexane. The foregoing bromoalkanes are commercially available.

Preferred bromoalcohols are of the formula $(Br)_a(H)_b(R^{30})_cC$—$C(H)_d(R^{31})_eOH$ where a is 1, 2, or 3; c is 0 or 1; a+b+c=3; d is 1 or 2; d+e=2; and $R^{30}$ and $R^{31}$ are the same or different and selected from the group consisting of hydrogen, alkyl having 1 to 18 carbon atoms, cycloalkyl, substituted alkyl, hydroxyalkyl, aryl, and substituted aryl and when a=3 and d=e=1, $R^{31}$ may also be OH or $OR^{32}$ wherein $R^{32}$ is alkyl having 1 to 18 carbon atoms, cycloalkyl, substituted alkyl, and hydroxyalkyl. More preferred bromoalcohols include 2,2,2-tribromoethanol; 2,2-dibromoethanol; 2-bromoethanol; 1,4-dibromo-2,3-butanediol; 2,3-dibromo-1,4-butanediol; 1,4-dibromo-2-butanol; 1,3-dibromopropanol; 2,3-dibromopropanol; 2,2,2-tribromo-1,1-dihydroxyethane; and 2,2,2-tribromo-1-methoxyethanol. Many of the foregoing bromoalcohols are commercially available.

Preferred chloroalcohols are of the formula $(Cl)_a(H)_b(R^{33})_cC$—$C(H)_d(R^{34})_eOH$ where a is 1, 2, or 3; c is 0 or 1; a+b+c=3; d is 1 or 2; d+e=2; and $R^{33}$ and $R^{34}$ are the same or different and selected from the group consisting of hydrogen, alkyl having 1 to 18 carbon atoms, cycloalkyl, substituted alkyl, hydroxyalkyl, and aryl and when a=3 and d=e=1, $R^{34}$ may also be OH or $OR^{35}$ wherein $R^{35}$ is alkyl having 1 to 18 carbon atoms, cycloalkyl, substituted alkyl, and hydroxyalkyl. More preferred chloroalcohols include 2,2,2-trichloroethanol; 2,2-dichloroethanol; 2-chloroethanol; 1,3-dichloro-2-propanol; 1,4-dichloroethanol; 2,3-butanediol; 1,4-dichloro-2-butanol; 2,2-dichloro-1-pentanol; 1,1-dichloro-2-pentanol; 1-chloropentanol; 2-chloro-1-pentanol; 2-chloro-1-phenylethanol; 1-chloro-1-phenyl-2-propanol; 2,2,2-trichloro-1,1-dihydroxyethane; and 2,2,2-trichloro-1-methoxyethanol. Some chloroalcohols are commercially available.

The preferred di(hydroxyalkyl)ester of tetrabromophthalic acid is PHT4-DIOL® which is the (2'-hydroxyethoxy) ethyl, 2-hydroxypropyl mixed ester of tetrabromophthalic acid and is available from Great Lakes Chemical Corporation.

Preferably, the additive is present at an amount of at least about 0.5 part by weight per hundred parts of polyol. More preferably, the additive is present at an amount of about 0.5 part to about 6 parts by weight per hundred parts of polyol. The additive is introduced preferably by dissolution in the blowing agent, in the polyol, in a mixture of two or more of the components, or it can be added as a separate stream at the point of mixing in the polymerization process. Thus, the present invention also provides a composition comprising hydrohalocarbon blowing agent, polyol, at least one catalyst, surfactant, and additive wherein the combination of the catalyst and additive is capable of resulting in a decreased amount of decomposition of hydrohalocarbon to haloalkenes.

The beneficial effect of the combination of catalyst and additive in polyurethane foam formulations is realized during the polymerization reaction within the normal processing time and temperature conditions occurring during typical foam blowing conditions, and especially during foam use at elevated temperatures.

The present invention also provides a process for preparing polyurethane foams. The process comprises the step of reacting polyol with polyisocyanate in the presence of hydrohalocarbon blowing agent, at least one catalyst, surfactant, and additive. The combination of the catalyst and the additive is capable of resulting in a decreased amount of decomposition of hydrohalocarbon to haloalkenes during polymerization of the isocyanate and the polyol and especially during foam use at elevated temperatures. The present invention also provides polyurethane foams prepared by the foregoing process. The present invention further provides polyurethane articles prepared by the foregoing process.

This invention is more fully illustrated by the following non-limiting examples in which parts or percentages are by weight unless otherwise specified.

The polyols used in the Comparatives and the Examples are in Table II below.

TABLE II

| POLYOL | AROMATIC AMINE POLYOL | SUCROSE POLYETHER POLYOL | TRADENAME | SOURCE |
|---|---|---|---|---|
| A | X | — | P-824® | BASF |
| B | X | — | M-4063® | MOBAY |
| C | — | X | P-975® | BASF |

COMPARATIVES AND EXAMPLES

Baseline data for the behavior of HCFC-141b, in the most commonly used formulations in polyurethane foams was established. The foams were prepared and analyzed as described hereafter.

The "hand mix" procedure, to be described, follows commonly accepted practices used for experimental evaluations in the rigid polyurethane foam industry. The polyol, 200 grams, was weighed into a quart container followed by the appropriate quantities of catalyst(s), surfactant, and blowing agent. This mixture of all formulation components, excluding the reactive polyisocyanate, is known to the industry as the B-side of the foam formulation. This B-side blend was thoroughly mixed for 10 seconds using a Jiffy speed mixer. Excessive whipping in air was avoided and any blowing agent that was lost during the mixing was replaced. The required amount of polyisocyanate was then added with thorough mixing at approximately 2200 revolutions per minute for 10 seconds. The mixture was poured rapidly into a 25.4 cm×25.4 cm×10.2 cm cakebox. The foam was then cured overnight at room temperature. The cured rigid foam was sampled by a specific cutting technique that provided four foam strips measuring 1 cm×1 cm×9 cm, from the center of the foam bun. The four strips were placed in an 8 oz. screw cap bottle which was then sealed with a #10130 MININERT® push-button gas chromatographic sampling valve available from Pierce Chemical Co.

An initial sample bottle was set aside at room temperature for one day prior to analysis. Other identical sample bottles were immediately stored in ovens maintained at 54° C. and were subsequently analyzed at an appropriate storage interval.

The absolute amounts of haloalkenes formed in foams blown with HCFC-141b may be determined using capillary gas chromatography as outlined in Table III below.

TABLE III

| CHROMATOGRAPH: | HEWLETT-PACKARD 5890 |
|---|---|
| CARRIER GAS: | HELIUM |
| INJECTOR: | CAPILLARY: CAPABLE OF 50:1 SPLIT |
| DETECTOR: | FID |
| COLUMN: | DB-1301 FUSED SILICA, 120 m × 0.25 mm, 1 μm FILM. AVAILABLE FROM J&W |

Three accurately prepared standards of the compounds of interest covering the ranges expected in the samples were prepared in the same type bottle used for the samples. Standards were prepared and analyzed daily.

The operating parameters are in Table IV below.

TABLE IV

| CARRIER FLOW RATE: | HEAD PRESSURE 40 PSIG, He |
|---|---|
| INJECTOR TEMPERATURE: | 150° C. |
| DETECTOR TEMPERATURE: | 250° C. |
| COLUMN CONDITIONS: | 20° C. FOR 15 MIN. 5° C./MIN. TO 40° C. |
| HOLD: | 5 MINUTES, 15° C./MIN. TO 230° C. |
| HOLD: | 30 MINUTES |
| INJECTION SIZE: | 2.0-ML VIA GAS TIGHT SYRINGE. |

Samples were received in 250-ml glass screw top bottles sealed with the previously described Mininert® Valves.

This method was used to separate and quantify the compounds in Table V below. RT means retention time and is in minutes.

TABLE V

| COMPOUND | STRUCTURE | RT |
|---|---|---|
| 1131a | $CH_2=CClF$ | 12.71 |
| 141B | $CCl_2F-CH_3$ | 23.82 |

All standards and samples were injected as vapor (gas) via a gas tight syringe. Calibration graphs of weight vs. peak were constructed. The peak area from the sample was determined and converted to weight via the calibration graph.

The weight of each component was taken from the calibration graphs. The equation is as follows:

$$\frac{\mu g \text{ component}}{g\text{-}HCFC\text{-}141b} = \frac{\mu g\text{-component from curve}}{g\text{-}HCFC\text{-}141b \text{ from curve}}$$

The quantities of polyol, blowing agent, catalyst, and surfactant were used as indicated in Table VI. The quantity of polyisocyanate was varied slightly in order to meet the stoichiometric requirements of the various polyols. In Table VI, the surfactant was Tegostab®B-8404 obtained from Goldschmidt Chemical Co. The polyisocyanate was Lupranate M-20S® obtained from BASF Corporation. The components are indicated in parts by weight.

TABLE VI

| COMPONENT | WT(PBW) |
|---|---|
| Polyol | 100 |
| Surfactant | 2 |
| Polyisocyanate | For Polyol A, 102 |
|  | For Polyol B, 125 |
| HCFC-141b | 35 |

The results of tests, using the aromatic amine polyols, are summarized in Table VII. For Comparatives A through D, the catalyst used was N,N-dimethylcyclohexylamine obtained from Air Products and Chemicals, Inc. as POLYCAT 8®. For Comparatives B and D, the ratio of water to HCFC-141b was 1 part water to 25 parts HCFC-141b. For Comparatives B and D, we did not age the samples and analyze for HCFC-1131a because the initial amount of HCFC-1131a was so high. For Example 1, the catalyst used was pentamethyldiethylene triamine, which has a boiling point of 220° C., obtained from the Rhein-Chemie Division of Mobay as DESMORAPID-PV®. In Example 1, water was present as a co-blowing agent in an amount of 1.5 gram/100 grams polyol and the hydrohalocarbon blowing agent, HCFC-141b, was reduced from 35 grams to 23 grams. We believe that the presence of water did not contribute to the effectiveness of the present invention.

TABLE VII

|  | COMP A | COMP B | COMP C | COMP D | EX 1 |
|---|---|---|---|---|---|
| POLYOL | A | A | B | B | B |
| CATALYST | POLYCAT-8 ® | POLYCAT-8 ® | POLYCAT-8 ® | POLYCAT-8 ® | D-PV ® |
| (g/100 g POLYOL) | (1.5) | (1.5) | (2) | (2) | (0.9) |
| HCFC-1131a (ug/g 141b) INITIAL | 3100 | 8070 | 170 | 360 | 90 |
| HCFC-1131a (ug/g 141b) AGED AT 54° C.(DAYS) | 6200(66) | — | 2300(66) | — | 210(85) |

The results of tests, using the sucrose polyether polyols, are summarized in Table VIII. For Comparatives E and F, the catalyst used was N,N-dimethylcyclohexylamine obtained from Air Products and Chemicals, Inc. as POLYCAT 8® (abbreviated P-8 in Table VIII). For Example 2, the catalyst (abbreviated CAT 2 in Table VIII) used was dibutyltin dilaurate, which is a non-volatile salt, obtained from Air Products and Chemicals, Inc. as DABCO T-12®. For Example 3, the catalyst (abbreviated CAT 3 in Table VIII)

used was $C_6H_5CH_2N(CH_3)_2$ which has a boiling point of 184° C. For Example 4, the catalyst (abbreviated CAT 4 in Table VIII) was $C_6H_5N(CH_3)_2$ which has a boiling point of 194° C. For Example 5, the catalyst (abbreviated CAT 5 in Table VIII) used was 2,4,6-tris($\underline{N},\underline{N}$-dimethylaminomethylphenol), which is a tertiary amine having —OH as an isocyanate-reactive functionality, obtained from Air Products and Chemicals Inc. as DABCO TMR-30®. For Example 6, the catalyst (abbreviated CAT 6 in Table VIII) was $(CH_3)_2NCH_2CH_2OH$ which is a tertiary amine having —OH as an isocyanate-reactive functionality. The molar ratio of amine on the catalyst to the starting materials remained the same for Comparative F and Examples 3 through 5.

TABLE VIII

|  | COMP E | COMP F | EX 2 | EX 3 | EX 4 | EX 5 | EX 6 |
|---|---|---|---|---|---|---|---|
| POLYOL | C | C | C | C | C | C | C |
| CATALYST (g/100 g Polyol) | P-8 (2.5) | P-8 (0.8) | CAT 2 (0.25) | CAT 3 (0.8) | CAT 4 (0.76) | CAT 5 (0.56) | CAT 6 (4.5) |
| HCFC-1131a (ug/g 141b) initial | 210 | 73 | 50 | 40 | 50 | 60 | 210 |
| HCFC-1131a (µg/g 141b) aged at 54° C. (days) | 2000 (58) | 1010 (114) | 50 (84) 50 (162) | 180 (122) 180 (199) | 90 (92) 60 (163) | 100 (92) 110 (206) | 80 (117) |

The results of tests, using aromatic amine polyols, are summarized in Table IX. For Example 7, the catalyst (abbreviated CAT 7 in Table IX) used was $\underline{N},\underline{N}$-dimethylaniline which has a boiling point of 194° C. For Example 8, the catalyst (abbreviated CAT 8 in Table IX) used was dibutyltin dilaurate which is a non-volatile salt. For Example 9, the catalyst used was $\underline{N},\underline{N}$-dimethylbenzylamine which has a boiling point of 184° C.

TABLE IX

|  | EX 7 | EX 8 | EX 9 |
|---|---|---|---|
| POLYOL | B | B | B |
| CATALYST (g/100 g POLYOL) | CAT 7 (5) | CAT 8 (0.1) | CAT 9 (5) |
| HCFC-1131a (ug/g 141b) INITIAL | 20 | <20 | 67 |
| HCFC-1131a (µg/g 141b) AGED AT 54° C.(DAYS) | <20 (31) | <20 (31) | 344 (38) |
| HCFC-1131a (µg/g 141b) AGED AT 93° C.(DAYS) | 169 (42) | 225 (42) | — |

The results of tests, using aromatic amine polyols, are summarized in Table X. For Example 10, the catalyst (abbreviated CAT 10 in Table X) used was a mixture of $\underline{N},\underline{N}$-dimethylaniline and dibutyltin dilaurate; the additive (abbreviated ADD 1 in Table X) was diethoxylated propoxylated diester of tetrabromophthalic acid which is available from Great Lakes Chemical Corporation as PHT4-DIOL®. For Example 11, the catalyst (abbreviated CAT 11 in Table IX) used was dibutyltin dilaurate which is a non-volatile salt; the additive (abbreviated ADD 2 in Table X) was 2,2,2-trichloroethanol.

TABLE X

|  | EX 10 | EX 11 |
|---|---|---|
| POLYOL | B | B |
| CATALYST (g/100 g POLYOL) | CAT 10 (5/0.1) | CAT 11 (0.1) |
| ADDITIVE (PPHP) | ADD 1 (5) | ADD 2 (1.1) |
| HCFC-1131a (ug/g 141b) INITIAL | <20 | <20 |
| HCFC-1131a (µg/g 141b) AGED AT 54° C.(DAYS) | 25 (35) | — |
| HCFC-1131a (µg/g 141b) AGED AT 93° C.(DAYS) | 221 (43) | 156 (27) |

Having described the invention in detail and by reference to preferred embodiments thereof, it will be apparent that modifications and variations are possible without departing from the scope of the invention defined in the appended claims.

What is claimed is:

1. A composition comprising polyisocyanate, polyol, hydrofluorocarbon blowing agent, surfactant, and at least one catalyst for polymerization of said polyisocyanate and said polyol wherein said catalyst is a polyamine of the formula $R^{16}R^{17}N-R^{18}-N(R^{19})-R^{18}-NR^{16}R^{17}$ wherein $R^{16}$, $R^{17}$, and $R^{19}$ are the same or different and selected from hydrogen or straight chain and branched alkyl having 1 to 18 carbon atoms; cycloalkyl having 5 to 18 carbon atoms; straight chain or branched substituted alkyl and hydroxyalkyl having 2 to 18 carbon atoms containing —$CH_2$—$CR^4R^5Cl$ where $R^4$ and $R^5$ are the same or different and selected from hydrogen, bromine, chlorine, aryl, or alkyl having 1 to 8 carbon atoms or straight chain or branched alkoxyalkyl having 4 to 23 carbon atoms containing —$CH_2$—$(CH_2)_n$—$(CO)_a$—$O$—$CH_2$—$CR^4R^5Cl$ where $R^4$ and $R^5$ are the same or different and selected from hydrogen, bromine, chlorine, aryl, or alkyl having 1 to 8 carbon atoms, n is 1 to 3, a is 0 or 1, $R^{18}$ is selected from alkyl having 1 to 18 carbon atoms; and said catalyst results in a decreased amount of decomposition of said hydrofluorocarbon blowing agent to haloalkenes.

2. A composition comprising polyisocyanate, polyol, hydrofluorocarbon blowing agent, surfactant, and at least one catalyst for polymerization of said polyisocyanate and said polyol wherein said catalyst is of the formula 2,4,6-tris ($\underline{N},\underline{N}$-dialkylaminomethylphenol) wherein said alkyl is selected from hydrogen or alkyl having 1 to 18 carbon atoms and said catalyst results in a decreased amount of decomposition of said hydrofluorocarbon blowing agent to haloalkenes.

3. A composition comprising polyisocyanate, polyol, hydrofluorocarbon blowing agent, surfactant, and at least one catalyst for polymerization of said polyisocyanate and said polyol wherein said catalyst is a hydroxyalkylamine and said catalyst results in a decreased amount of decomposition of said hydrofluorocarbon blowing agent to haloalkenes.

4. The polyurethane composition of claim 1 wherein said catalyst is selected from the group consisting of hydroxyalkylamines of the formula $R^{20}R^{21}N$—$CH_2$—$CH(R^{22})(OH)$ where $R^{20}$ and $R^{21}$ are the same or different and selected from straight chain or branched alkyl or substituted alkyl or hydroxyalkyl having 1 to 18 carbon atoms; straight chain or branched substituted alkyl having 2 to 18 carbon atoms containing —$CH_2$—$CR^4R^5Cl$ where $R^4$ and $R^5$ are the same or different and selected from hydrogen, bromine, chlorine, aryl, or alkyl having 1 to 8 carbon atoms, or straight chain or branched alkoxyalkyl having 4 to 23 carbon atoms containing —$CH_2$—$(CH_2)_n$—$(CO)_a$—O—$CH_2$—$CR^4R^5Cl$ where $R^4$ and $R^5$ are the same or different and selected from hydrogen, bromine, chlorine, aryl, or alkyl having 1 to 8 carbon atoms, n is 1 to 3, and a is 0 or 1; and $R^{22}$ is selected from straight chain or branched alkyl or hydroxyalkyl having 1 to 18 carbon atoms or straight chain or branched substituted alkyl having 6 to 18 carbon atoms containing —$CH_2$—$CR^4R^5Cl$ where $R^4$ and $R^5$ are the same or different and selected from hydrogen, bromine, chlorine, aryl, or alkyl having 1 to 8 carbon atoms, or straight chain or branched alkoxyalkyl having 4 to 23 carbon atoms containing —$CH_2$—$(CH_2)_n$—$(CO)_a$—O—$CH_2$—$CR^4R^5Cl$ where $R^4$ and $R^5$ are the same or different and selected from hydrogen, bromine, chlorine, aryl, or alkyl having 1 to 8 carbon atoms, n is 1 to 3, and a is 0 or 1.

5. A composition comprising polyisocyanate, polyol, hydrofluorocarbon blowing agent, surfactant, and at least one catalyst for polymerization of said polyisocyanate and said polyol wherein said catalyst is pentamethyldiethylene triamine; dibutyltin dilaurate; $C_6H_5CH_2N(CH_3)_2$; $C_6H_5N(CH_3)_2$; 2,4,6-tris-(N,N-dimethylaminomethylphenol); or $(CH_3)_2NCH_2CH_2OH$ and said catalyst results in a decreased amount of decomposition of said hydrofluorocarbon blowing agent to haloalkenes.

6. A polyurethane composition comprising polyisocyanate, polyol, hydrofluorocarbon blowing agent, surfactant, and at least one polyamine catalyst of the formula 2,4,6-tris(N,N-dialkylaminomethylphenol) wherein alkyl is selected from hydrogen or alkyl having 1 to 18 carbon atoms for polymerization of said polyisocyanate and said polyol wherein said polyamine catalyst results in a decreased amount of decomposition of said hydrofluorocarbon blowing agent to haloalkenes.

7. The polyurethane composition of claim 6 wherein said polyamine catalyst is 2,4,6-tris(N,N-dimethylaminomethylphenol).

8. A process for preparing polyurethane foam comprising the step of: reacting polyol with polyisocyanate in the presence of hydrofluorocarbon blowing agent, surfactant, and at least one polyamine catalyst of the formula 2,4,6-tris (N,N-dialkylaminomethylphenol) wherein said alkyl is selected from hydrogen or alkyl having 1 to 18 carbon atoms for polymerization of said polyol and said polyisocyanate wherein said polyamine catalyst results in a decreased amount of decomposition of said hydrofluorocarbon blowing agent to haloalkenes.

9. The process of claim 8 wherein said polyamine catalyst is 2,4,6-tris(N,N-dimethylaminomethylphenol).

* * * * *